(12) United States Patent
Hellenkamp

(10) Patent No.: US 6,296,649 B1
(45) Date of Patent: *Oct. 2, 2001

(54) AUTOMATIC SURGICAL DEVICE FOR CUTTING A CORNEA

(76) Inventor: Johann F. Hellenkamp, 7740 SW. 75 Terr., Miami, FL (US) 33143

(*) Notice: Subject to any disclaimer, the term of this patent is extended or adjusted under 35 U.S.C. 154(b) by 0 days.

This patent is subject to a terminal disclaimer.

(21) Appl. No.: 08/840,430

(22) Filed: Apr. 29, 1997

Related U.S. Application Data

(63) Continuation of application No. 08/598,180, filed on Feb. 7, 1996, now Pat. No. 5,624,456.

(51) Int. Cl.[7] ................................................ A61F 9/007
(52) U.S. Cl. ........................................................ 606/166
(58) Field of Search ........................... 606/166, 167, 606/5

(56) References Cited

U.S. PATENT DOCUMENTS

| | | |
|---|---|---|
| Re. 35,421 | 1/1997 | Ruiz et al. . |
| 3,583,403 | 6/1971 | Pohl et al. . |
| 4,173,980 | 11/1979 | Curtin . |
| 4,205,682 | 6/1980 | Crock et al. . |
| 4,429,696 | 2/1984 | Hanna . |
| 4,660,556 | 4/1987 | Swinger et al. . |
| 4,662,370 | 5/1987 | Hoffmann et al. . |
| 4,665,914 | 5/1987 | Tanne . |
| 4,674,503 | 6/1987 | Peyman et al. . |
| 4,688,570 | 8/1987 | Kramer et al. . |
| 4,807,623 | 2/1989 | Lieberman . |
| 4,884,570 | 12/1989 | Krumeich et al. . |
| 4,903,695 | 2/1990 | Warner et al. . |
| 4,943,296 | 7/1990 | Funakubo et al. . |
| 4,997,437 | 3/1991 | Grieshaber . |
| 5,108,412 | 4/1992 | Krumeich et al. . |
| 5,133,726 | 7/1992 | Ruiz et al. . |
| 5,215,104 | 6/1993 | Steinert . |
| 5,288,292 | 2/1994 | Giraud et al. . |
| 5,318,044 | 6/1994 | Kilmer et al. . |
| 5,368,604 | 11/1994 | Kilmer et al. . |
| 5,395,385 | 3/1995 | Kilmer et al. . |
| 5,403,335 | 4/1995 | Loomas et al. . |
| 5,464,417 | 11/1995 | Eick . |
| 5,486,188 | 1/1996 | Smith . |
| 5,586,980 | 12/1996 | Kremer et al. . |
| 5,591,174 | * 1/1997 | Clark et al. ............................ 606/166 |
| 5,964,748 | * 10/1999 | Peyman .................................. 606/166 |

OTHER PUBLICATIONS

Steinway Instrument Company, Inc., "The Steinway/Barraquer In-Situ Microkeratome Set" Brochure.

"New Methods in Refractive Corneal Surgery—An Experimental Study," by J. Draeger et al., Klin. Mbl. Augenheilk, 192 (1988), pp. 458–461.

"A Semi–Automatic Electric Keratome for Lamellar Corneal Graft," by J. Draeger, Klin Mbl Augenheilk, 167 (1976), pp. 353–359.

"Lamellar Refractive Keratoplasty," Bores Eye Institute, 1988, 1989, Chapter 4, pp. 1–9.

* cited by examiner

Primary Examiner—Michael H. Thaler
(74) Attorney, Agent, or Firm—Malloy & Malloy, P.A.

(57) ABSTRACT

A surgical device for cutting substantially across a cornea of an eye of a patient, the device including a positioning ring structured to be temporarily attached to a portion of the eye surrounding the cornea to be cut, and defining an aperture sized to receive and expose the cornea to be cut. The surgical device further includes a cutting head assembly structured to be guided and driven over an upper surface of the positioning ring in a generally arcuate path, and having a cutting element positioned therein and structured to oscillate laterally to facilitate smooth and effective cutting of the cornea. The cutting head assembly is structured to be detachably coupled to the positioning ring while simultaneously permitting movement of the cutting head assembly relative to the positioning ring along the generally arcuate path.

15 Claims, 7 Drawing Sheets

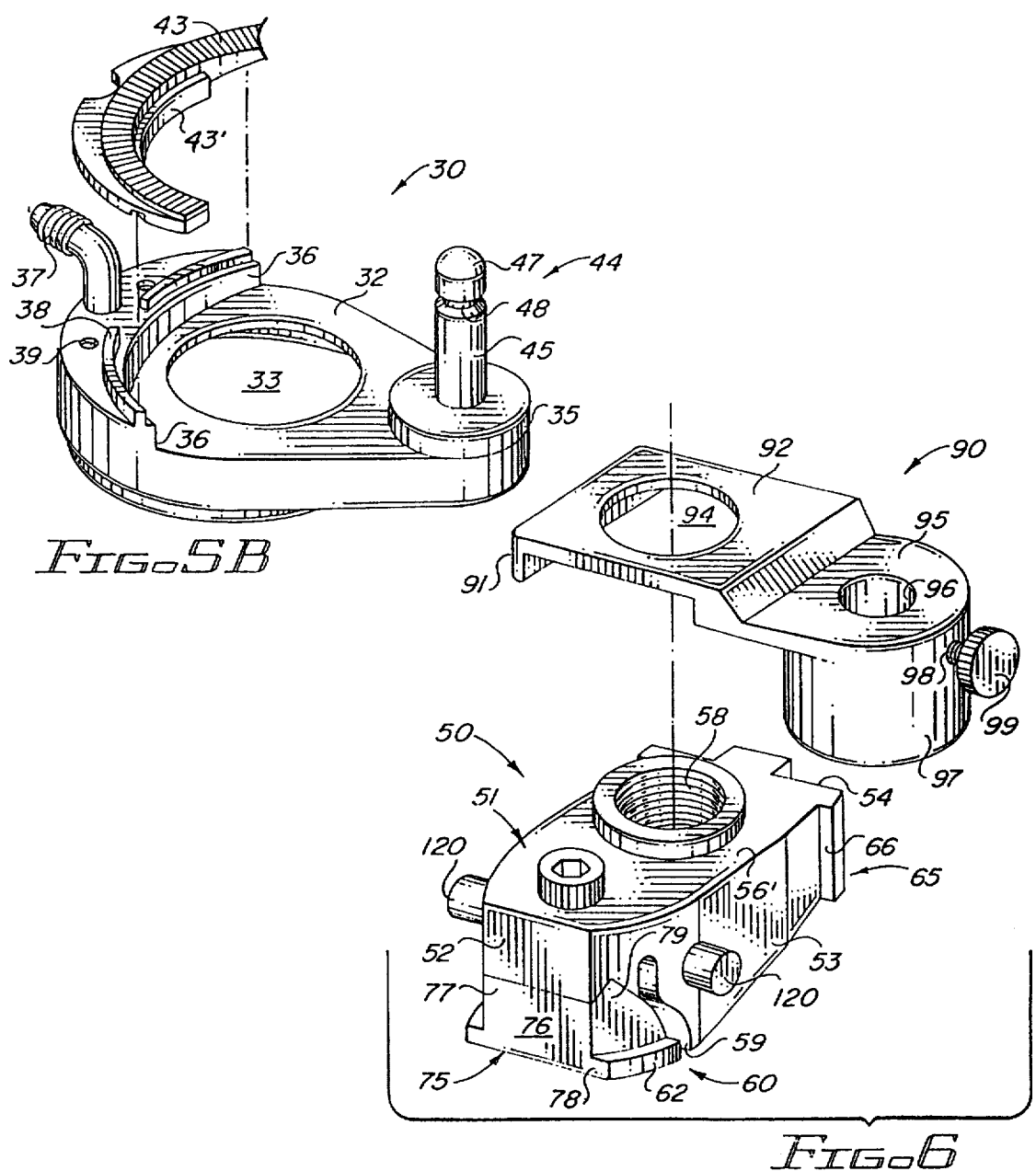
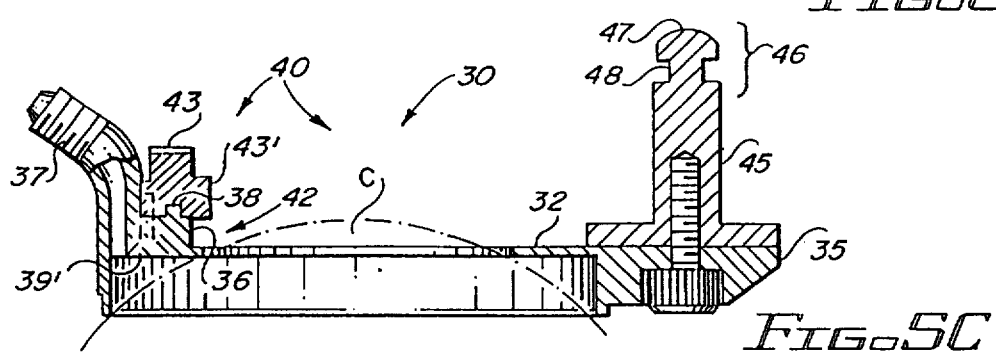

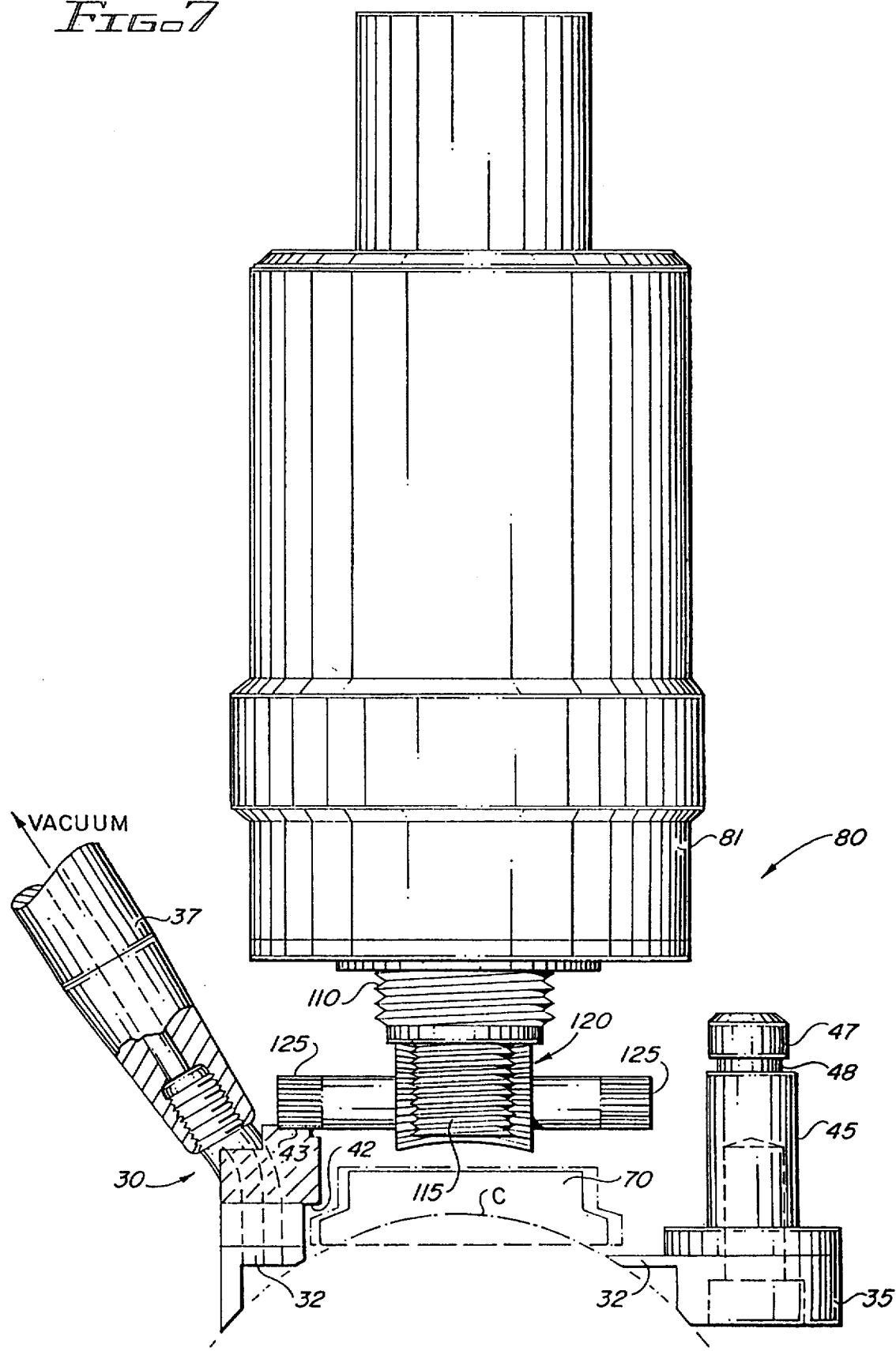

START

50%

FINISH

AUTOMATIC SURGICAL DEVICE FOR CUTTING A CORNEA

This application is a continuation of application Ser. No. 08/598,180, filed Feb. 7, 1996, now U.S. Pat. No. 5,624,456.

BACKGROUND OF THE INVENTION

1. Field of the Invention

The present invention relates to a medical apparatus used during the performance of eye surgery. In particular, the present invention is directed towards an automatic surgical device for cutting the cornea of a patient's eye and creating a hinged flap of corneal tissue. More particularly, the automatic surgical device of this invention includes a cutting head assembly which is specifically structured to move across the patient's eye along a generally arcuate path, and further, is readily usable on both eyes of the patient.

2. Description of the Related Art

The eye works on a principle very similar to that of a camera and is illustrated generally in FIG. 1. The iris I, or colored portion of the eye about the pupil P, functions like a shutter to regulate the amount of light admitted to the interior of the eye. The cornea C or clear window of the eye, and the lens L, which is located behind the pupil, serve to focus the light rays from an object being viewed onto the retina R at the back of the eye. The retina then transmits the image of the object viewed to the brain via the optic nerve, O. Normally, these light rays will be focused exactly on the retina, see dashed lines in FIGS. 2 and 3, which permits the distant object to be seen distinctly and clearly. Deviations from the normal shape of the corneal surface, however, produce errors of refraction in the visual process so that the eye becomes unable to focus the image of the distant object on the retina. As one example, illustrated in FIG. 2, hyperopia or "farsightedness" is an error of refraction in which the light rays from a distant object are brought to focus at a point behind the retina, as indicated by the solid lines. As another example, illustrated in FIG. 3, myopia or "nearsightedness" is an error of refraction in which the light rays from a distant object are brought to focus in front of the retina, as indicated by the solid lines, such that when the rays reach the retina, R, they become divergent, forming a circle of diffusion and consequently, a blurred image.

Until about twenty years ago, such refractive errors could only be treated with eyeglasses or contact lens, both of which have well known disadvantages for the user. As one example, a patient having a large degree of refractive error will commonly be prescribed to wear a very thick and cumbersome pair of glasses, which the patient should wear at all times to correct his/her extremely poor vision. As another example, contact lenses, which are designed to fit directly over the cornea, can be difficult to insert and remove, and in any event, must be carefully cleaned and cared for. Even then, contact lenses may at times irritate the eyes of those patients who can wear them.

Consequently, in the last several years, research has been directed to surgical operations to change the refractive condition of the eye. Several methods and special instruments have been designed for performing this kind of surgery. One such technique was keratomileusis, developed by Dr. Jose Barraquer of Colombia in 1949, which required a precise reshaping of the cornea. The goal of corneal reshaping is to modify the curvature of the cornea, i.e., either to flatten or increase its curvature depending on the patient's condition, with the desired result being that light rays passing through the cornea will then be refracted to converge directly onto the retina. Keratomileusis was extremely difficult to perform because it required cutting the cornea to separate and remove a thin layer or section of corneal tissue from a patient's eye, termed the corneal cap, precise lathing of it into a new shape, and then replacing it and suturing it back onto the patient's cornea.

Keratomileusis has been abandoned in recent years to eliminate the requirement of lathing the corneal tissue and suturing it back into place. Automated Lamellar Keratectomy (ALK) is another surgical technique which developed as an outgrowth of keratomileusis, wherein the eye is first numbed by a drop of anesthetic, and then a suction ring is placed on the eye to carefully position the cornea (termed "centration" in the art) for being cut by a very fine microsurgical instrument known as a microkeratome. The microkeratome is generally a blade carrying device that must be manually pushed or mechanically driven in a cutting path across the suction ring simultaneous with the motorized movement of the cutting element, which movement is transverse to the direction of the cutting path. For treating myopia pursuant to ALK procedures, the microkeratome is typically used to first cut into the cornea so as to raise a thin layer of the anterior cornea of between 100–200 microns in depth and about 7 millimeters in diameter. Next, the microkeratome is then used to make a second pass over the cornea to resect or remove a smaller part of the cornea, generally about 4 to 6 millimeters in diameter, which is then discarded. The anterior corneal cap which was cut away with the first pass of the microkeratome is then put back into its original position, without suturing, for healing to occur. The desired result of this procedure is that the cornea will have a new curvature because of the resected tissue, which provides a new refracting surface to correct the patient's original myopic condition. To correct hyperopia under ALK however, the microkeratome is typically used to make a single deep pass over the cornea. The cut layers are put back into their original position, without any removal of any other tissue. Because of the depth of the cut, the intraocular pressure within the eye causes a steepening of the cornea to again, provide a new refracting surface which hopefully will correct the patient's original hyperopic condition.

In recent years, it has been learned that in using the microkeratome to cut and separate a thin layer of the cornea, termed the anterior corneal cap, it is highly undesirable to completely separate this cap from the rest of the cornea. First, the corneal cap has been lost in some instances which is calamitous because the anterior segment of the eye must then be completely reconstructed. Second, it is also now known that following the reshaping of the cornea, the corneal cap should be carefully and precisely aligned back into its original position on the cornea; failure to do so may result in astigmatism or some unbeknownst refractive error. Consequently, it is now understood that the microkeratome should not sever the cap from the eye but instead, should leave a portion connected or "hinged" to the eye, thereby forming a raised layer of corneal tissue hinged to the eye, known as a corneal flap F, illustrated in FIG. 4. A significant problem however, is that presently known microkeratome devices do not readily permit the formation of a corneal flap, F. Instead, known microkeratomes involve a degree of guesswork for determining where on the eye to stop cutting movement of the microkeratome across the cornea so as to form the corneal flap. Further, there are multiple issues that a surgeon needs to consider in corneal flap construction, the three most important factors being: flap thickness, flap size and hinge size.

Another advance has been made in more recent years in surgical procedures to correct refractive errors of the eye, namely, the introduction of laser procedures to accomplish the reshaping of the cornea. One such procedure, known as Laser Intrastromal Keratomileusis, (LASIK), is currently considered optimal because it allows sculpting of the cornea without damaging adjacent tissues. Moreover, with the aid of computers, the laser can be programmed by a surgeon to precisely control the amount of tissue removed, and significantly, to permit more options for the reshaping of the cornea. Under LASIK procedures, the eye is still typically positioned within a suction ring and a microkeratome is typically used to cut into the cornea so as to raise a thin layer of the cornea. As described, it is now preferred that a corneal flap be formed. Significantly, it has been determined that the corneal flap should have a depth of no less than 130 microns and no more than 160 microns to yield optimal results. It should be borne in mind that achieving this result during surgery requires an extremely precise instrument as one micron is a unit of length equal to one thousandth of a millimeter. During laser surgery, the flap of corneal tissue is then gently pushed aside to expose and permit reshaping of the cornea by the laser. Consequently, the microkeratome is less frequently used to reshape the cornea, as occurred under ALK procedures, but is still used to cut into and to raise a thin layer of corneal tissue. A significant problem however, is that presently known microkeratome devices do not offer the degree of precision currently needed to properly and consistently form a corneal flap, instead of a corneal cap, let alone a corneal flap having a dimension within the range of currently desirable depth and a vastly improved smooth cut. Further, it has been determined that a larger diameter of the eye should be presented, as much as 8 to 10 millimeters, for corneal reshaping by the laser. This is because the laser can now be used to re-shape the corneal surface about a perimeter of the eye rather than at the center, which is believed to result in more accurate correction of refractive errors. Doing so however, requires that a sufficiently large diameter of the eye be presented and exposed, which is not possible to achieve with known microkeratome devices. For example, known suction rings for positioning the eye during surgery would likely require a greatly expanded frame, and that that frame be located lower on and about the girth of the eyeball, in order to expose a greater portion thereof. Such an assembly would likely be very difficult to employ given the physical space limitations of the eye socket.

Finally, known microkeratome devices typically cut across the cornea in a linear direction along a horizontal plane. That is, known microkeratome devices typically cut across the cornea in a direction starting from the side of the eye near the temple, proceeding horizontally across the face towards the nose. As a result, even if such microkeratomes were able to be effectively used to construct a corneal flap, let alone one of the currently desired more precise dimensions, the hinged portion of the corneal flap would be oriented at right angles to the natural blinking action of the patient, which is in the vertical plane. It is believed that it would be most optimal to construct a corneal flap having a hinged portion which is oriented to correspond with the natural blinking action of the patient in the vertical plane. It is however, believed that known microkeratomes cannot move linearly in a vertical plane because of the restrictions presented by the size of the eye socket formed by the cheek and brow bones of the human skull.

Thus, there is a need for an improved automated microkeratome which automatically and consistently permits the formation of a corneal flap, and which allows for even more precise construction of the corneal flap so as to result in a flap thickness of no less than 130 microns and no more than 160 microns, and a flap size between 8 and 10 millimeters in diameter. There is also a need for an improved automated microkeratome which more smoothly cuts across the cornea in forming the corneal flap so as to permit it to be precisely aligned back into its original position on the cornea following the reshaping of the cornea. Ideally, any such improved automated microkeratome will also permit construction of the corneal flap in such a way that the hinged portion of the flap will be oriented to correspond the natural blinking of the eye.

SUMMARY OF THE INVENTION

The present invention is designed to satisfy the needs in the art and is directed towards a new and improved automatic surgical device known as a microkeratome. The improved microkeratome of the present invention is adapted to cut and raise a thin layer of the cornea of a patient's eye and to create a hinged flap of corneal tissue. The present invention is seen to comprise means for retaining and positioning the eye on which surgery is to be performed, a cutting head assembly including a cutting element positioned therein for cutting the cornea of the eye, and a coupling member for detachably coupling the retaining and positioning means and cutting head assembly while permitting movement of the cutting head assembly relative to the retaining and positioning means along a generally arcuate path.

In the preferred embodiment, the retaining and positioning means comprise a positioning ring having means for temporary attachment to a portion of the eye surrounding the cornea to be cut, and which expose and present the cornea for cutting. The positioning ring includes guide means thereon, preferably disposed on an upper surface thereof and extending in a generally arcuate path.

The cutting head assembly of the present invention is structured and disposed to be at least partially received in the guide means of the retaining and positioning means and to be driven substantially but not completely over the cornea of the eye so as to cut the cornea and form a corneal flap. The cutting head assembly is also structured and disposed to be guided by the guide means on the retaining and positioning means along a generally arcuate path during movement of the assembly there across. The cutting head assembly is seen to comprise a main housing which carries a cutting element positioned therein and disposed for cutting and raising the corneal flap. In the preferred embodiment, the cutting head assembly includes a flap receiving gap formed within an under surface thereof forward of the cutting element for protectively receiving the corneal flap of tissue formed by the forward movement of the cutting head assembly. Further, the cutting head assembly is structured and disposed to be movably coupled to the positioning ring by way of a coupling member which detachably couples the cutting head assembly and the positioning ring and yet, permits movement of the cutting head assembly relative to the positioning ring along a generally arcuate path. The present invention further comprises driving means for driving the cutting head assembly over the retaining and positioning means, and in the preferred embodiment, includes stop means, which are structured and disposed to limit movement of the cutting head assembly across the retaining and positioning means. The stop means may be formed on the cutting head assembly and may be structured and disposed to engagingly abut the guide means of the retaining and positioning means so as to limit further movement of the cutting head assembly at a point before the cutting element has passed completely over the cornea of the eye, thereby forming a corneal flap on the eye undergoing surgery. In the preferred embodiment, the drive means are operably connected to the cutting head assembly at a top surface thereof and are capable of stopping and reversing the direction of movement of the cutting head assembly once the stop means have prevented movement of the cutting head assembly in a first direction across the retaining and positioning means.

A primary object of the present invention is to provide an improved automated surgical device, for cutting and raising a thin layer of tissue from the cornea of an eye undergoing surgery, without completely severing the layer from the cornea of the eye, thereby creating a corneal flap.

Another primary object of the present invention is to provide an improved automated surgical device which forms a corneal flap wherein the hinged portion of the flap is oriented so as to cooperate with the blinking of the eye, and thereby, assist proper repositioning and alignment of the corneal flap on the cornea following surgery.

It is also an object of the present invention to provide an improved automated surgical device which permits a surgeon to more precisely and consistently construct a corneal flap and to obtain a flap thickness of not less than 130 microns and not more than 160 microns.

A feature of the present invention is that it permits a surgeon to expose a diameter of the cornea which is between 8 to 10 millimeters, and ideally about 9.5 millimeters, so as to permit the construction of a relatively large diameter flap size which is preferable in reshaping a cornea utilizing laser procedures.

Another object of the present invention is to provide an improved automated surgical device which more smoothly cuts across the cornea in forming the corneal flap so as to permit the flap to be more precisely aligned back into its original position on the cornea following the reshaping of the cornea.

A further object of the present invention is to provide an improved automated surgical device which can be readily used on either a patient's left or right eye.

Still another object of the present invention is to provide an improved automated surgical device having a center of gravity during operation which is substantially centered over the patient's eye.

An additional object of the present invention is to provide an improved automated surgical device which exposes and permits cutting of a larger diameter across the eye without a greatly expanded assembly for positioning the eye.

Yet another object of the present invention is to provide an improved automated surgical device which as a result of its arcuate path of travel, facilitates the formation of a larger diameter cut to the cornea, without having to locate the assembly positioning the eye to a lower position about the eye.

BRIEF DESCRIPTION OF THE DRAWINGS

For a fuller understanding of the nature of the present invention, reference should be had to the following detailed description taken in connection with the accompanying drawings in which:

FIG. 5-B is an exploded perspective view of a preferred embodiment of the retaining and positioning means according to the present invention, which include a positioning ring having guide means and a toothed track;

FIG. 5-C is a cross sectional view of the retaining and positioning means shown in FIG. 5-B;

FIG. 6 is an exploded perspective view of the cutting head assembly according and the coupling member according to the present invention;

FIG. 7 is a side view of the present invention in assembled form and in position on a patient's cornea;

FIGS. 9-A, 9-B and 9-C are partial, cross sectional views taken along the plane of the arrowed lines 9—9 of FIG. 8, and illustrating sequential views during the cutting of the cornea in which:

FIG. 9-A illustrates the cutting head assembly in an initial position in contacting relation with the positioning ring and the guide means thereon;

FIG. 9-B illustrates the cutting head assembly moving through an intermediate position where cutting of the cornea occurs;

FIG. 9-C illustrates the cutting head assembly in a movement stopped position wherein the abutting or stop means are in contacting relation with the guide means of the positioning ring;

FIG. 10-B is also a front schematic illustration of the present invention in use on both a patient's left and right eyes and depicting the cutting head assembly in the movement stopped position, wherein a corneal flap has been formed with the resulting hinged portion being oriented so as to cooperate with the blinking of the eye following surgery.

Like reference numerals refer to like parts throughout the several views of the drawings.

DETAILED DESCRIPTION OF THE PREFERRED EMBODIMENT

Figure 10A:
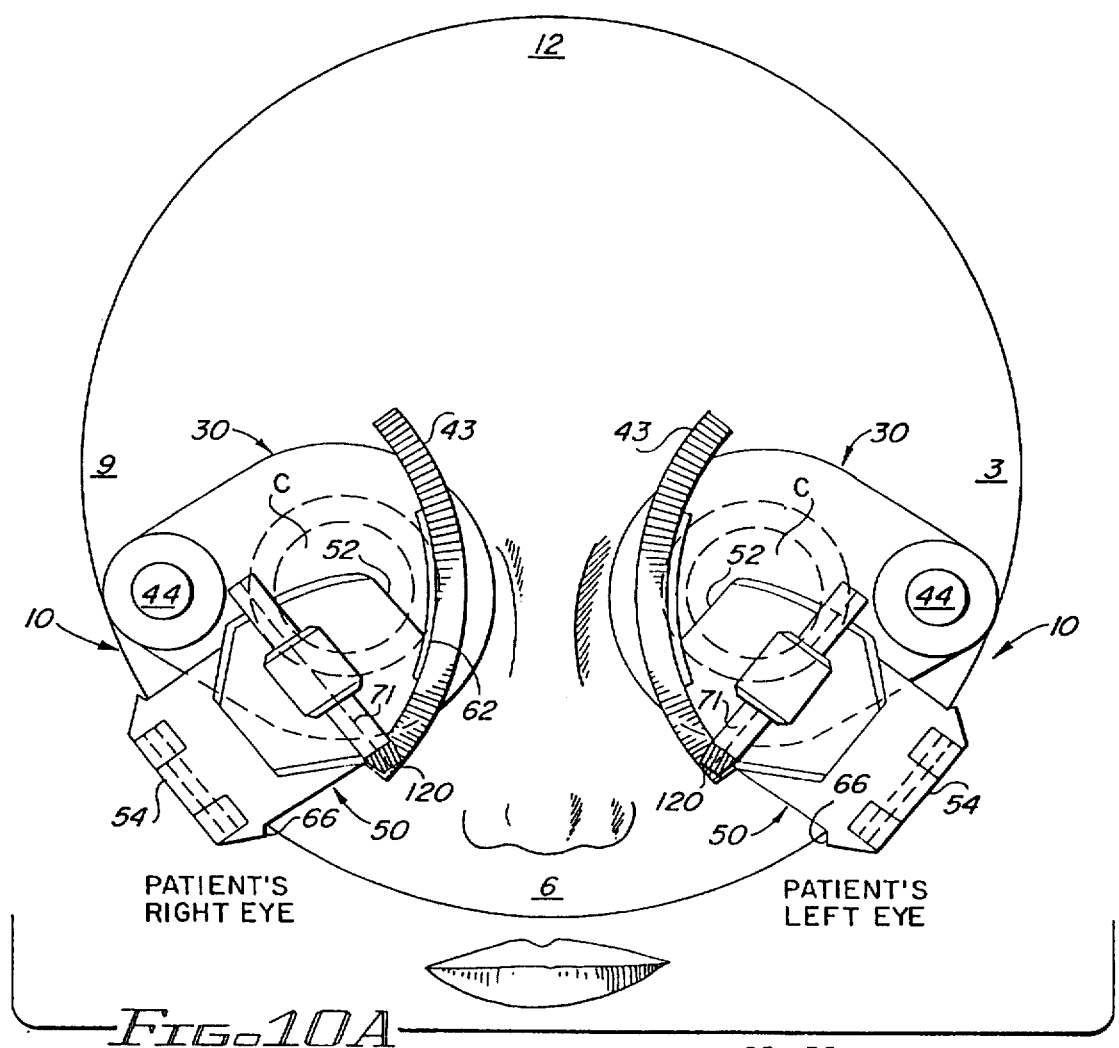
FIG. 10-A is a front schematic illustration of the present invention in use on both a patient's left and right eyes and illustrating the cutting head assembly in the initial position.
Figure 10B:
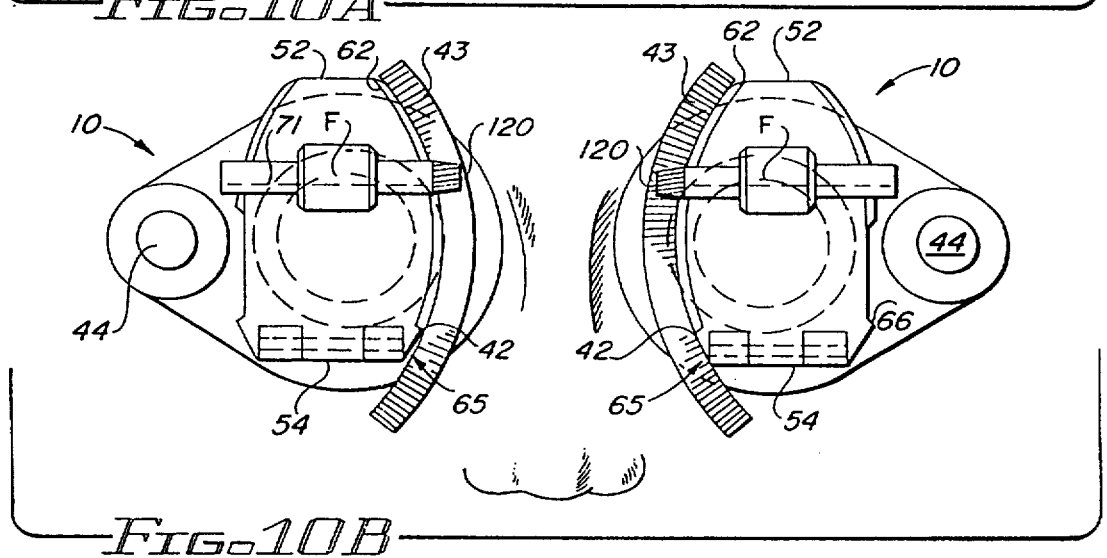

Illustrated throughout the drawings, the present invention is a mechanical apparatus used in the performance of surgery on the eye, and is generally indicated as 10 in FIGS. 10-A and 10-B. More specifically, the invention is directed towards an automatic surgical device, known as a microkeratome, to be utilized on an eye which is about to undergo surgery to correct refractive errors of the eye such as hyperopia, myopia or astigmatism. The improved microkeratome of the present invention is structured to cut substantially but not completely across the cornea of a patient's eye so as to raise a thin layer thereof and create a hinged flap of corneal tissue. The hinged portion of corneal tissue created by the present invention is also oriented so as to cooperate with the blinking of the eye following surgery.

Figure 5A:
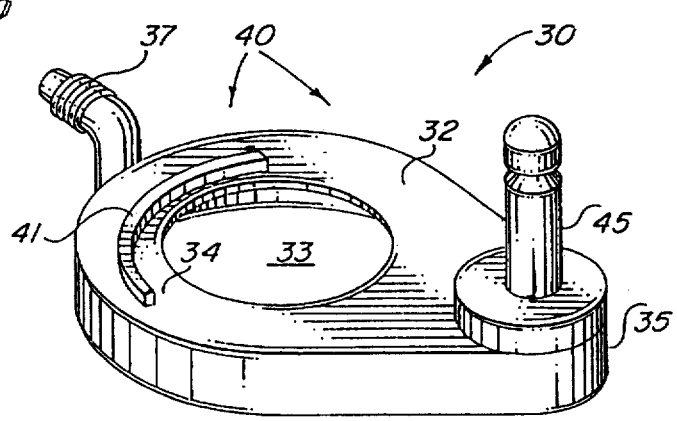
FIG. 5-A is a perspective view of an embodiment of the retaining and positioning means according to the present invention, namely a positioning ring.

Referring now to FIGS. 5-A, 5-B, and 5-C, the device 10 includes means 30 for retaining and positioning the eye on which surgery is to be performed. The retaining and positioning means 30, which may be made of high grade stainless steel, preferably comprise a positioning ring 32 having an aperture 33 formed therein. The aperture 33 is sized to permit the cornea C, of the eye to pass therethrough and be exposed, as depicted in FIG. 5-C. In the preferred embodiment, and as illustrated in the drawings, positioning ring 32 is defined by a generally tear-drop shape, which is readily suited for accommodating the movement of a cutting head assembly, 50, discussed below, along an arcuate path, and further, which is structured and disposed to present the cornea so that a diameter of generally about 8 to 10 millimeters may be cut. The positioning ring 32 could, however, be formed to have another shape and still function for the intended purpose.

Positioning ring 32 further includes means for being temporarily attached to a portion of the eye surrounding the cornea on which surgery is to be performed. Ideally, the temporary attachment means include suctioning means. For example, positioning ring 32 preferably includes a connection member 37, which as illustrated in FIG. 5-C, is in fluid communication with an under surface of positioning ring 32. Connection member 37 is adapted to be interconnected with a vacuum hose (not shown) which in turn may be connected to a vacuum means (also not shown) such that when suction occurs, the under surface of positioning ring 32 forms a seal about and is retained about the cornea portion of the eye which is about to undergo surgery. Further, the structure of positioning ring 32, accompanied by the suctioning, acts to properly position the cornea C, for surgery and to maintain the position during surgery as well. Typically, a vacuum of about 25 inches of Hg at sea level will be used.

The retaining and positioning means 30 further include guide means or a guide assembly 40 formed thereon. Guide means 40 may be formed directly on the positioning ring 32, so as to be integral therewith, or may be operably connected thereto as a separate element. In any event however, the guide means 40 will be disposed on positioning ring 32 so as to guide and facilitate movement of the cutting head assembly 50, discussed below, during the surgical cutting of the cornea. Referring to FIGS. 5-A and 5-C, in the preferred embodiment, guide means 40 are seen to comprise a channel member 41, 42, which extends along a length of at least one side of positioning ring 32 and preferably, on an upper surface of positioning ring 32. It will also be appreciated from the drawings that channel member 41, 42 extends across ring 32 in an arcuate or semi-circular path. As depicted in FIG. 5-A, channel member 41 may comprise an elongated, generally "C" shaped structure or even an inverted "L" shaped structure, which is operably connected to an upper surface of ring 32, such as designated by numeral 34. As illustrated in FIGS. 5-B and 5-C however, in the most preferred embodiment channel member 42 is formed by the interconnection of two separate elements, namely, an upwardly and arcuately extending sidewall 36 formed on positioning ring 32, and a toothed track 43 which is interconnected with sidewall 36. Still referring to FIG. 5-C, in the most preferred embodiment, positioning ring 32 is seen to include the upwardly and arcuately extending sidewall 36 having a ridge 38 formed on an upper surface thereof, and extending partially if not completely along, at least one side of positioning ring 32. Further, in this preferred embodiment, the toothed track 43 is structured to be operably connected to ridge 38 by way of mating structure. For example, the mating structure can be in the form of a receiving groove disposed on the under surface of toothed track 43, and/or by way of conventionally known fasteners 39' such as screws, rivets, etc. which may pass through positioning ring 32 at apertures 39 and extend into toothed track 43. As further illustrated in FIG. 5-C, toothed track 43 is seen to include a lip 43' which is sized and dimensioned to protrude beyond the vertical plane formed by sidewall 36. Thus, guide means 40 in the form of a generally "C" shaped channel member 42 is comprised by the combined structure of sidewall 36 and toothed track 43, having lip 43'. With respect to the embodiment shown in FIG. 5-A, it is contemplated that a toothed track may also be mounted to an upper surface of positioning ring 32 or to an upper surface of channel member 41. It will be appreciated that toothed track 43 cooperates with the drive means 80 (see FIGS. 7 and 11) so as to drive the cutting head assembly 50 across positioning ring 32, as more fully discussed below.

In a preferred embodiment, the guide means 40 further comprise a rigid upstanding member 44 disposed on the retaining and positioning means 30, and generally opposite the toothed track 43. As will again be appreciated from the drawings, in the preferred embodiment, wherein positioning ring 32 is of a tear-drop shape, rigid upstanding member 44 comprises a post member 45 securely connected to positioning ring 32 on an upper surface thereof at or near a tip 35 thereof. From the explanation which follows, it will become clear that channel member 42 and rigid upstanding member 44 permit the cutting head assembly 50 of the invention, in a preferred embodiment, to become effectively guided and securely received on the positioning ring 32 in two places while still permitting cutting head assembly 50 to be smoothly and slidably moved over positioning ring 32 along a generally arcuate path, by way of a pivoting motion about rigid upstanding member 44. Of course, the positioning ring could be formed to include another channel member, such as 41, 42, which extends along a length of the other side of positioning ring 32, also preferably, on an upper surface thereof, so as to also permit the cutting head assembly 50 of the invention to become effectively guided and securely received on the positioning ring 32 in two places while still permitting the cutting head assembly 50 to be smoothly and slidably moved over positioning ring 32 along a generally arcuate path.

Referring now to FIG. 6, the present invention is seen to include a cutting head assembly 50. A primary purpose of the cutting head assembly 50 is to house a cutting element 70, see FIG. 8, with a cutting surface operatively exposed therefrom. As such, upon the cutting head assembly 50, with the cutting element 70, being moved across the cornea retained within positioning ring 32, the cornea may be precisely cut by cutting element 70. To accomplish this, cutting head assembly 50 includes a main housing 51 containing the cutting element 70. Additionally, included in the main housing 51 is an aperture 58 structured and disposed to permit drive means 80 to be operably connected thereto (see FIGS. 7 and 11) and to thereby drive the cutting head assembly 50 across positioning ring 32 in order to effectively cut the cornea. Further, as the cutting head assembly 50 must be driven in a smooth and controlled manner across the cornea, housing 51 includes tracking means 60 which are structured and disposed for mating communication with and tracking within channel member 42, of positioning ring 32, in order to precisely guide the cutting head assembly 50, and therefore the cutting element 70, along the defined arcuate path. Finally, as a significant feature of the present invention is to cut a portion of the cornea without completely severing it, abutting or stop means 65 are provided, which serve the purpose of limiting and preferably, completely stopping the movement of the cutting head assembly 50 from cutting completely across the cornea, that is, before the assembly has passed completely over the cornea. The abutting or stop means are preferably disposed on the main housing 51. These features will be discussed in more detail below.

Still referring to FIG. 6, the preferred embodiment of the present invention is also seen to include a coupling member 90. While the cutting head assembly 50 might be directly and yet movably engaged with the positioning ring 32 for performing an operation on the eye, preferably, a coupling member 90 is utilized as part of the invention, which is structured and disposed to movably couple the cutting head assembly 50 to the positioning ring 32 while simultaneously permitting movement of the cutting head assembly 50 relative to positioning ring 32. As illustrated in FIG. 6, coupling member 90 comprises two segments: a) a retaining segment 92 and b) a pivot segment 95. The retaining segment 92 is structured and disposed to be fitted onto a top wall surface 56' of main housing 51 and may include downwardly depending flanges 91, 93 to snugly receive and grip a portion of housing 51 therebetween. The retaining segment 92 also includes an aperture 94 formed therein to correspond to aperture 58 of housing 51. As such, aperture 94 is sized and configured to allow passage of the driving shaft of the driving means 80 (shown in FIGS. 7 and 11) therethrough and into aperture 58 of the housing 51. Thus, in assembled form, coupling member 90 is securely yet removably coupled to head assembly 50 as a result of the engagement of the driving means 80 with the housing 51 through retaining segment 92. Turning to the pivot segment 95 of coupling member 90, it is structured and disposed to be coupled to rigid upstanding member 44 of positioning ring 32 and to permit coupling member 90, and accordingly, the cutting head assembly 50 connected thereto, to pivotally move about post member 45. Preferably, pivot segment 95 includes a bushing 97 having a bore 96 formed therein, which is sized to receive a substantial height of post member 45, thereby captivating it therein. Further, in the preferred embodiment, the pivot segment 95 includes maintaining means 46, see FIG. 5-C, for maintaining rigid upstanding member 44 within bushing 97 and engagement means 98 for maintaining bushing 97 over rigid upstanding member 44. Referring now to FIGS. 5-B and 5-C, the maintaining means 46 preferably include an enlarged head 47 on rigid upstanding member 44, and an annular recess 48 or taper about the neck section of upstanding member 44. As illustrated in FIG. 6, the engagement means 98 preferably comprise a threaded shaft which passes through a sidewall of bushing 97 and can be selectively moved into engagement with upstanding member 44 by rotating handle 99 and causing a tip thereof to extend into the annular recess 48, thereby preventing removal of the pivot segment 95 from the upstanding member 44, when surgery is to take place. It will be therefore be appreciated that in assembled form, the engagement means 98 and maintaining means 46 cooperate to permit coupling member 90 and cutting head assembly 50 to rotate about upstanding member 44 while preventing bushing 97 from sliding up and off of upstanding member 44. It will also be appreciated that in assembled form, upstanding member 44 acts as additional guide means for enabling the cutting head assembly 50 to be driven along an arcuate path in a smooth and controlled manner across positioning ring 32 and thus, the cornea C.

Referring back to FIG. 6, as well as to FIGS. 7 and 8, the cutting head assembly 50 as well as its operation will now be described in more detail. As previously recited, the cutting head assembly 50 comprises the main housing 51 which includes a top surface 56', a bottom wall, and a surrounding sidewall structure 53 defining a front end face 52, and an oppositely disposed rear end face 54. Because during surgery, the cutting head assembly 50 is driven across positioning ring 32 along an arcuate path, front end face 52 preferably defines a tapered nose to cooperate with the arcuate path of channel member 42. Also as previously recited, the main housing is structured to contain the cutting element 70 and operatively expose a cutting surface thereof. In the preferred embodiment, the cutting head assembly 50 as well as the cutting element 70, are structured and disposed to permit a diameter of the cornea of generally about 8 to 10 millimeters to be cut, and ideally, about 9.5 millimeters. Although the cutting element 70 may be formed integrally with main housing 51, in the preferred embodiment the main housing 51 includes an interior chamber 88, see FIG. 8, structured to receive and maintain an independent cutting element 70 in a cutting position. Most preferably, the cutting element 70 is disposed within the main housing 51 at about 20 to 30 degrees from the horizontal plane. Also, a cutting opening 56 is formed at a bottom of housing 51 so as to expose a cutting surface of cutting element 70, see FIG. 8. In the preferred embodiment, cutting element 70 comprises a blade having a sharpened cutting edge 71, the cutting tip of which is preferably formed to have an angle of approximately and generally between 5 to 10 degrees from the horizontal axis of the blade, and further, the blade itself is operably connected to yet removable from, a blade holder 72. Blade holder 72 is operably connected to the drive means 80, see FIG. 11, connected to housing 51 through aperture 58, and drive means 80 impart an oscillating movement causing blade holder 72 and blade 71 to move back and forth generally between opposite walls of the surrounding sidewall structure 53 of housing 51. Accordingly, the interior chamber 88 within housing 51 will be sized to receive the cutting element or blade 70 and blade holder 72 and to permit the oscillating cutting movement of same within housing 51.

Additionally, in order to permit a used cutting element 70 to be removed and replaced, housing 51 includes access means 55. Although the access means 55 may include an exterior slot or like access, in the preferred embodiment, and as illustrated in FIG. 8, access means 55 at least partially form bottom wall of housing 51 near rear end face 54, and ideally, comprise a door member 57 which is hingedly connected to the surrounding sidewall structure 53 at rear end face 54. Door member 57 is movable between a closed operative position for surgery and an open position for permitting a used or contaminated cutting element 70 to be removed from the housing 51 and replaced with a new or sterile cutting element. Door member 57 may be selectively maintained in the closed position by conventionally known fasteners as depicted in FIG. 8. It will be appreciated from FIG. 8 that door member 57 does not completely bridge the cutting element 70. It is believed that this structure is sturdier and less fragile than the structure of known microkeratomes, which are prone to being bent if, when the cutting element is inserted, it is not properly aligned within the microkeratome.

Also, in the preferred embodiment, housing 51 of cutting head assembly 50 will include depth adjusting means 75 for adjusting the depth at which cutting element 70 cuts into the cornea. As illustrated in FIG. 8, the depth adjusting means 75 are preferably disposed at the front end face 52 of main housing 51 and form at least a portion of the bottom wall of housing 51 near front end face 52. Preferably, the depth adjusting means 75 comprise a separate nose segment 76, which is structured to be securely, yet removably interconnected with housing 51 by way of a conventionally known fasteners 74 such as a screw, a bolt, etc. Preferably, the nose segment 76 comprises an engagement segment 77 and a variable depth plate member 78. Engagement segment 77 preferably includes a terminal end 79 which is formed to define an inverted "V" shape, and preferably extends across the width of the nose segment 76. This structure is sized and configured to be received and to nest within a corresponding void, also shaped like an inverted "V" formed within housing 51 on and between oppositely disposed sidewall structures 53, adjacent front end face 52. It will be appreciated that this structure permits a highly stable nesting or dwelling of terminal end 79 within housing 51 even as the cutting head assembly 50 is moved along an arcuate path over positioning ring 32. Further, as illustrated, variable depth plate member 78 is preferably integral with engagement segment 77 and is disposed substantially in the horizontal plane. Variable depth plate member 78, has a depth depicted as "H" in FIG. 8, which is a dimension pre-selected by the surgeon to correspond the desired depth of the cut to be made into the cornea. A significant feature of the present invention is to provide a plurality of nose segments 76, each including a plate member 78 having a differently dimensioned depth "H". It will be appreciated from FIG. 8 that there is an inverse relationship between the depth of plate member 78 and the depth of the cut to the cornea as the cutting head assembly 50 proceeds forward during surgery in the direction of the arrow "A" and pushes down on the cornea. For example, a plate member 78 having a larger depth "H" will shield more of the blade's cutting edge 71 whereas a plate member 78 having a smaller depth "H" will expose more of area above the blade's cutting edge. It will thus be recognized that the cutting head assembly 50 is designed to be interchangeable with differently sized depth adjusting means 75 so as to precisely meet the needs of the patient undergoing surgery. Ideally, the present invention will offer two differently sized nose segments 76, namely one sized for 130 microns and another for 160 microns which are currently the most desirable depths for cutting into the cornea and exposing same for reshaping.

As has been described, housing 51 of cutting head assembly 50 also includes tracking means 60. Referring to FIG. 6, tracking means 60, which in the preferred embodiment are disposed on a lower peripheral zone of housing 51, are structured for mating communication with and tracking within channel member 42, see FIG. 5-C, of positioning ring 32. For example, tracking means 60 may comprise an outwardly extending flange disposed on a side of the housing 51, along the lower edge thereof, and may take the form of a continuous flange about the housing 51, or alternatively a plurality of pin members disposed thereabout. In the preferred embodiment however, the tracking means 60 are disposed on the depth adjusting means 75 and are integral with and planar to the variable depth plate member 78 in the form of a flange 62, see FIG. 6. Preferably, flange 62 extends out beyond the periphery defined by surrounding sidewall 53 of housing 51 in generally perpendicular relation thereto. Further, although the cutting head assembly 50 is designed to receive nose segments 76 having variable depth plate members 78, flange 62 which extends therefrom is of a uniform height so as to correspond and effect mating communication with and tracking within channel member 42, of positioning ring 32. Although flange 62 could extend only from one side of the housing 51, in the preferred embodiment, flange 62 is disposed on each side of variable depth plate member 78, thereby facilitating use of the present invention on either a patient's left or right eye.

Figure 1:
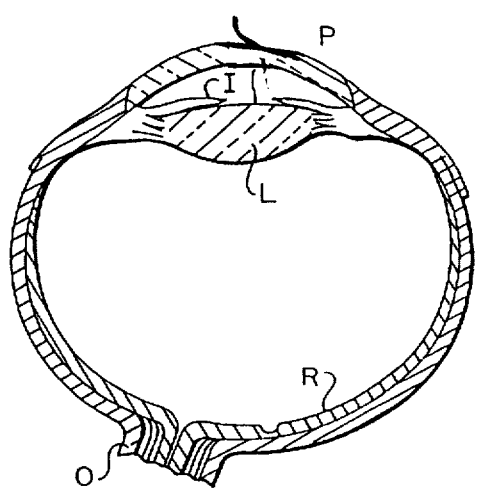
FIG. 1 is a schematic illustration of a horizontal section of the eye.
Figure 2:
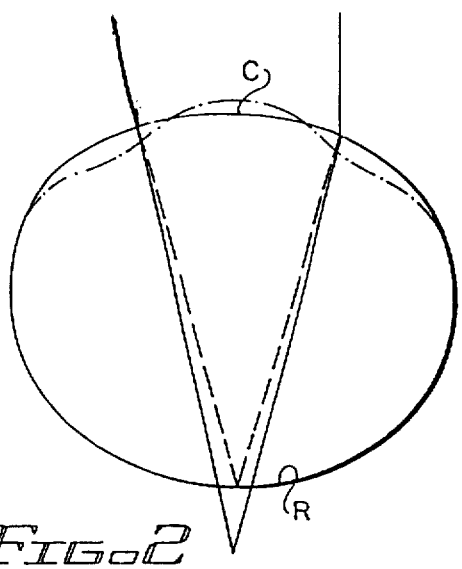
FIG. 2 is a schematic illustration of a hyperopic eye wherein refracted rays converge at a point behind the retina.
Figure 3:
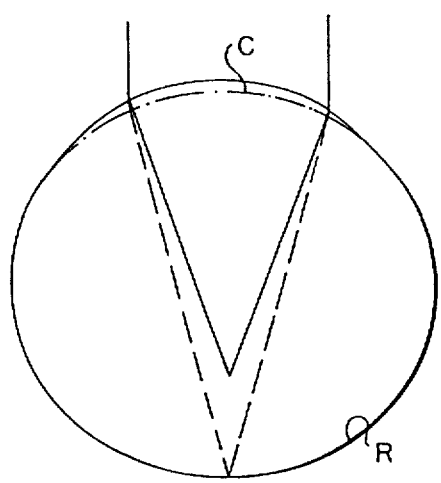
FIG. 3 is a schematic illustration of a myopic eye wherein refracted rays converge at a point which is short of the retina.
Figure 4:
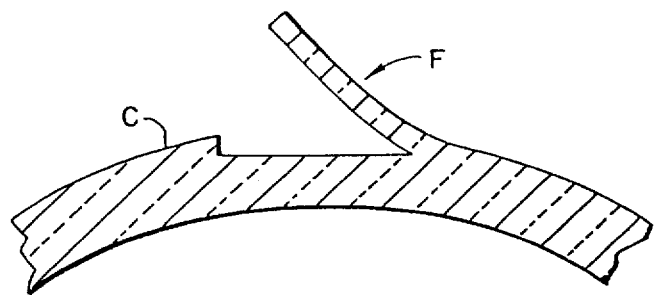
FIG. 4 is schematic illustration of a cornea of an eye wherein a corneal flap has been created.

Also as previously recited, the main housing 51 includes abutting or stop means 65 which serve the purpose of limiting and preferably stopping, the forward movement of cutting head assembly 50 across positioning ring 32. In the preferred embodiment, stop means 65 are formed generally at rear end face 54 on surrounding sidewall structure 53 and are seen to comprise a shoulder 66 formed at the juncture between sidewall structure 53 and rear end face 54 of the housing 51, which shoulder is sized to be too large to pass within the channel member 42 of the guide means 40, thereby preventing any further forward motion of the head assembly 50 across positioning ring 32. When abutting engagement occurs between shoulder 66 and channel member 42, by way of lip 43', the driving means 80 can be stopped and then reversed to permit movement of the cutting head assembly 50 in the opposite direction. As has been described, it has been determined in recent years that in performing surgery on the cornea, the layers of the cornea which are cut should not be completely severed. A unique feature of the cutting head assembly 50 and of this invention 10 is that the cutting of the cornea results in the formation of a corneal flap F, as illustrated in FIG. 4, which is also safely preserved by the assembly 50. To preserve the corneal flap F, housing 51 includes a flap receiving gap 59 formed within housing 51. As illustrated in FIG. 6 and more clearly in FIG. 8, flap receiving gap 59 is disposed generally near the front end face 52 of housing 51 and more particularly, is defined by a gap formed just forward of the blade's cutting edge 71 and just rearward of variable depth plate member 78. Thus, flap receiving gap 59 is disposed on an under surface of housing 51 and extends upwardly and into housing 51. Ideally, flap receiving gap 59 extends through the opposite sidewall structure 53 of housing 51.

Figure 8:
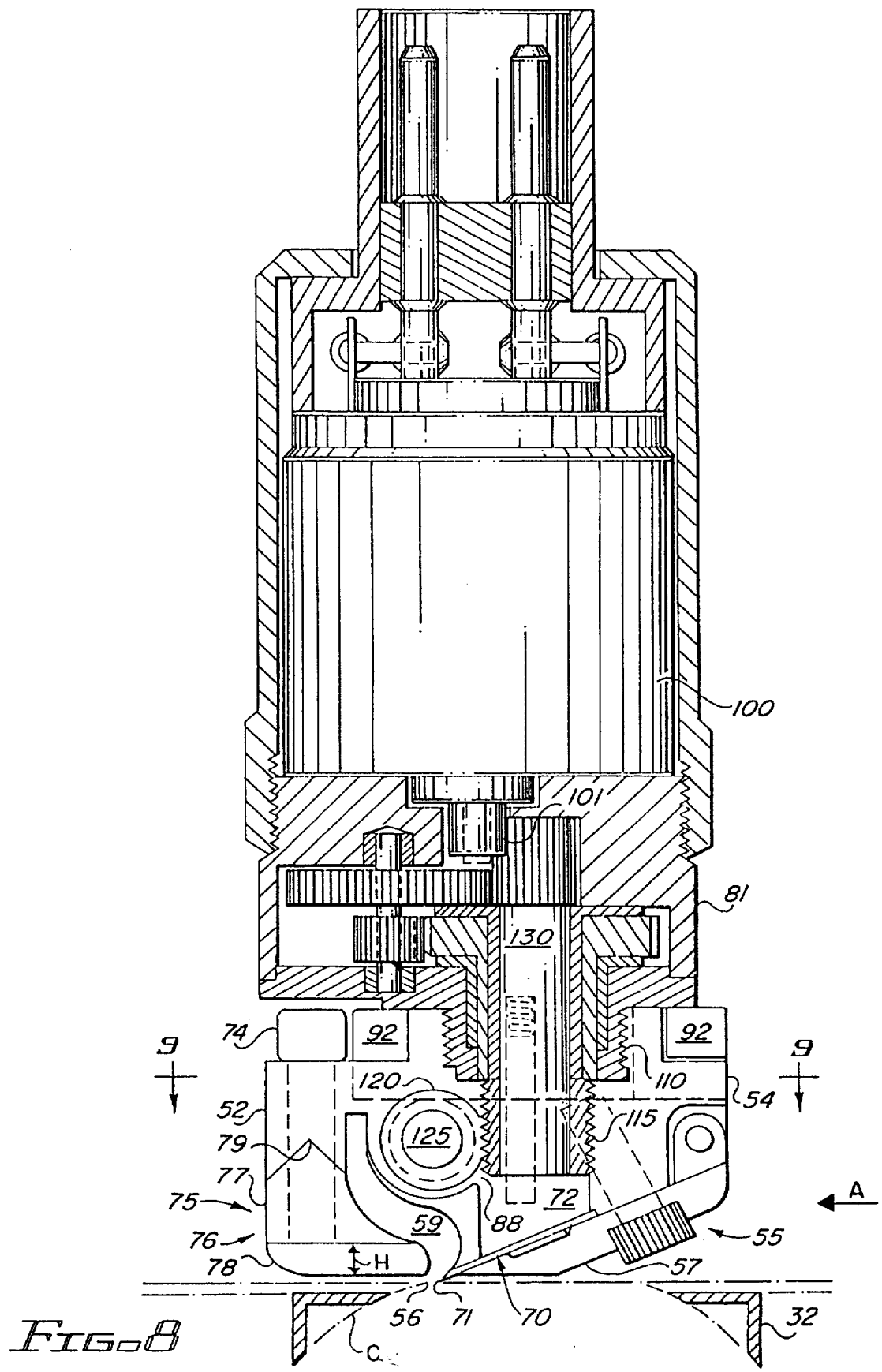
FIG. 8 is a partial cross sectional view of the present invention in assembled form and in position on a patient's cornea.
Figure 9A:
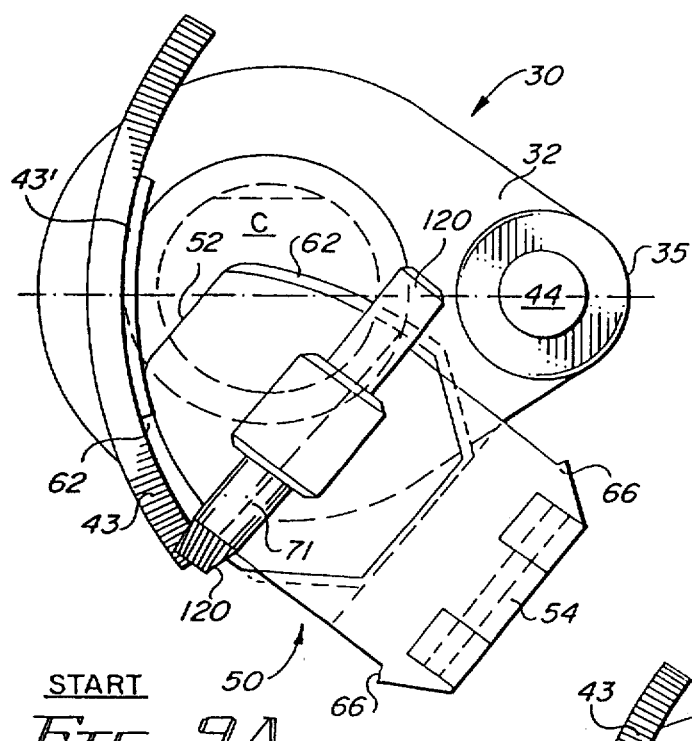
Figure 9B:
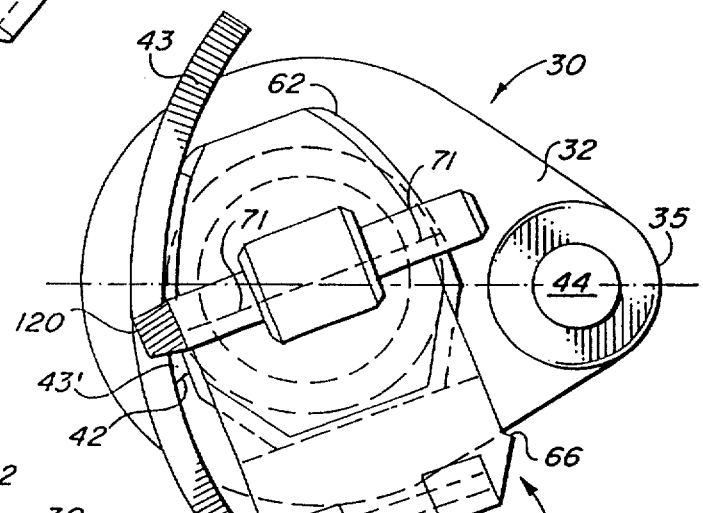
Figure 9C:
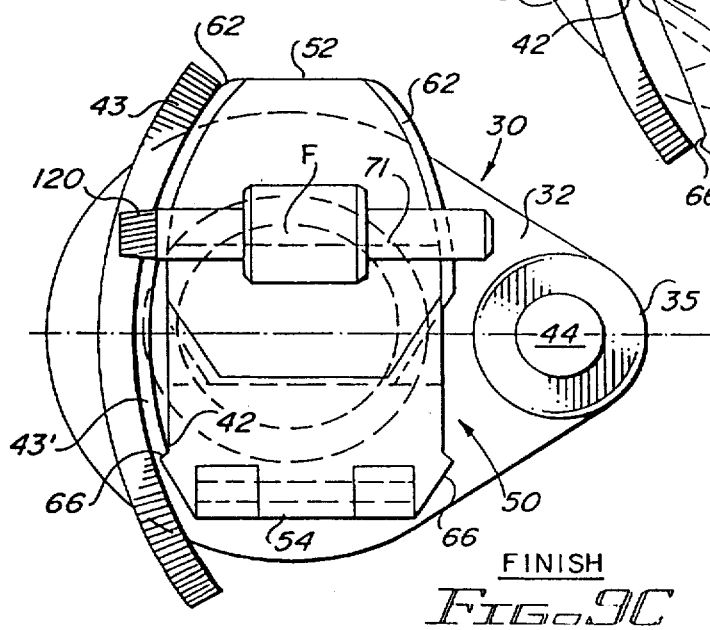

Referring now to FIGS. 9-A, 9-B and 9-C, the cutting head assembly is illustrated in sequential positions during its movement in a cutting path over the cornea being treated. As a preliminary step in the cutting the cornea, FIG. 9-A depicts a) the retaining and positioning means 30, and b) the cutting head assembly 50 coupled as previously described by coupling member 90, as the tracking means 60 of the head assembly 50 have been initially matingly connected to the guide means 40 of positioning ring 32. More specifically, it is seen in FIG. 9-A that first, a front end of flange 62 has been matingly received in channel member 42 of retaining ring 32 and also, that the worm gear 120 is alignedly received on toothed track 43 of positioning ring 32. Turning to FIG. 9-B, the cutting head assembly 50 has moved into position across the positioning ring and cutting of the cornea C is taking place. FIG. 9-C illustrates the cutting head assembly 50 in a position wherein the stop means 65 are contacting channel member 42 of the positioning ring 32, to limit and preferably, prevent any further forward motion of the assembly. It will also be clear from FIG. 9-C that in this stopped position, the cutting element 70 has not moved completely across the cornea C, but rather has cut a portion of the cornea up until this point, creating a corneal flap which is left attached to the cornea as designated by the area marked "F" which is shown in the FIG. 9-C. Moreover, as illustrated in FIG. 8, the corneal flap created has been directed by the forward movement of the assembly, upwardly and into flap receiving gap 59 of housing 51 to be preserved and kept clear of cutting element 70. Once the assembly has been stopped as in FIG. 9-C, the drive means 80 can be reversed to permit movement of the cutting head assembly 50 in the opposite direction, which does not result in any further cutting of the cornea, but rather, in the safe removal of the corneal flap F out of flap receiving gap 59 of housing 51. Thus, when head assembly 50 returns through to a position analogous to that shown in FIG. 9-A, the head assembly can be disconnected from the retaining means 30. The corneal flap F can then be maneuvered so as to permit the cornea to be reshaped, preferably by way of a laser surgical procedure. Once the surgery has been completed, the corneal flap is returned to a covering relation over cornea.

Another unique feature of the present invention is not only that a corneal flap can be created, but significantly, that the corneal flap is positioned in such a way that the blinking of the eye will not improperly position the corneal flap on the cornea following surgery. Referring now to FIGS. 10-A and 10-B, the invention is schematically illustrated on both a patient's left and right eyes. As depicted in FIG. 10-A, reference points of the work environment can be equated with the position of some numerals on the face of a clock. Thus, in FIG. 10-A, it will be noted that with respect to the patient's left eye, the cutting head assembly 50 in the initial position is preferably disposed at a generally five o'clock position. With respect to the patient's right eye, the cutting head assembly 50 in the initial position is preferably disposed at a generally seven o'clock position. Turning now to FIG. 10-B, the cutting head assembly 50 is shown to have moved towards a position generally aligned with the twelve o'clock position, wherein the stop means 65 are in abutting engagement with channel member 42 of the positioning ring 32, such that any further forward motion of the assembly is prevented. It will thus be appreciated that regardless of whether the surgical procedure is being performed on a patient's left or right eye, the cutting head assembly 50 is preferably aligned generally with a twelve o'clock position. It will also be appreciated from FIG. 10-B that the resulting corneal flap F, remains attached to the cornea at an upper region thereof. Consequently, following the surgical procedure to reshape the cornea, the orientation of the corneal flap will be in generally the same direction as the natural blinking action. That is, it is believed that the downward blinking motion of the patient will tend to stroke the corneal flap down and thereby assist with maintaining the corneal flap in proper re-position on the cornea so as to avoid the development of astigmatism.

Figure 11:
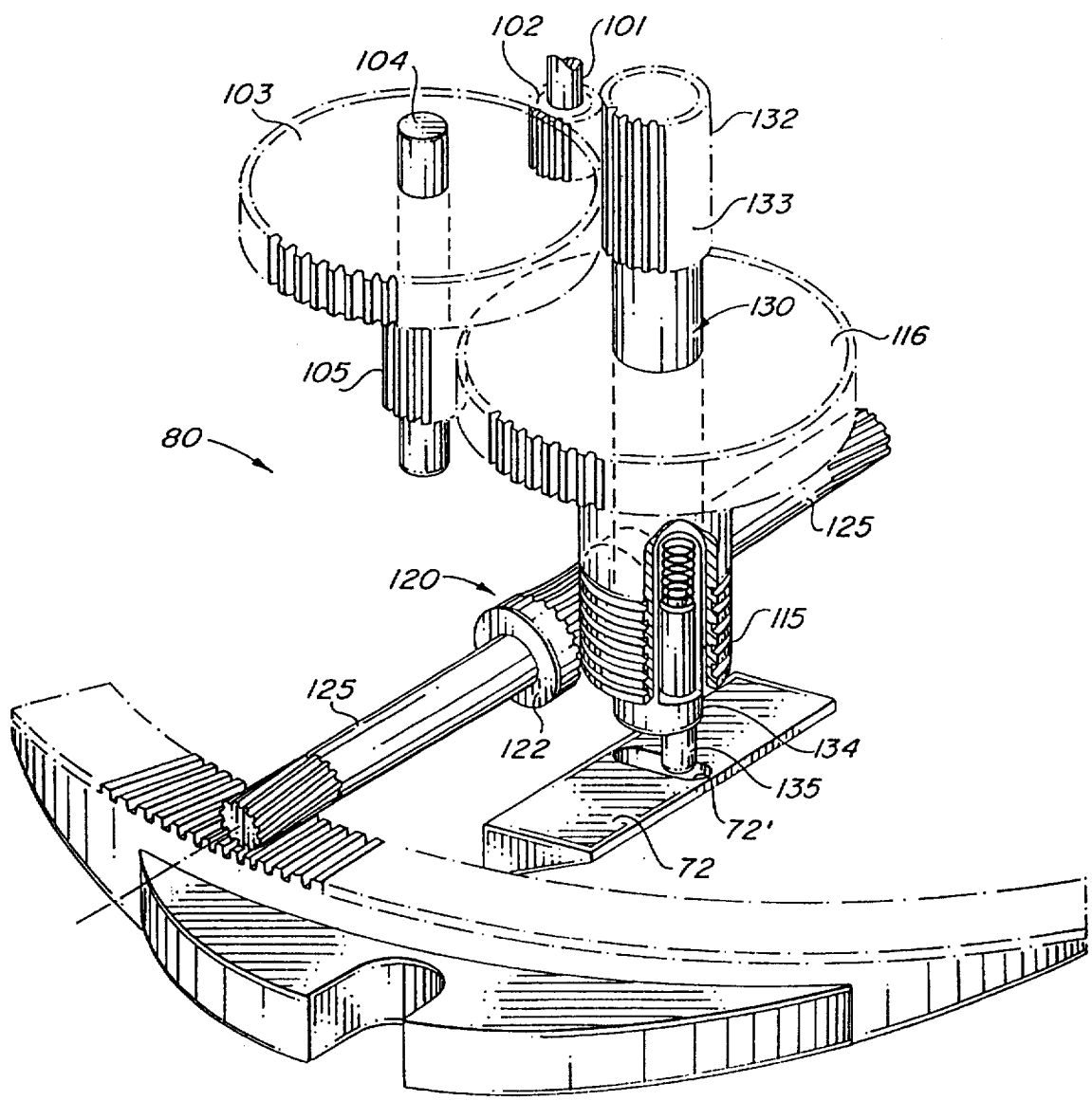
FIG. 11 is an isolated perspective view of the drive means illustrating the operation and interconnection of the worm, worm gear, and oscillating shaft.

Referring now to FIG. 11, the present invention includes drive means 80 both: a) for driving the cutting head assembly 50 across the previously described eyeball retaining and positioning means 30; and b) for causing the cutting element 70 to oscillate back and forth within housing 51. The driving means preferably include a motor 100, preferably electrically operated and most preferably, a micromotor capable of operating at a constant and uniform speed, regardless of the load. Specifically, under normal circumstances the natural resistance encountered by the cutting head assembly, as it is driven over the cornea, would result in an increased resistance in the winding of the micromotor, which would tend to cause a voltage drop and therefore a drop in speed. While some known systems attempt to avoid excessive drops in speed by incorporating an overpowered motor to keep losses below a 10% slow down, the motor 100 of the present invention is preferably equipped to monitor current flowing therethrough, such as using an op amp, and utilize that information to control the applied voltage and maintain the constant speed. This monitoring and compensation, sometimes referred to as I R compensation, thereby permits a conventional, regulated 12 V supply to be used with a DC motor in order to maintain the effective constant speed of travel over the eye.

Referring now to FIGS. 8 and 11, the driving means 80 further include a gear box 81 into which a motor main drive shaft 101 extends. From the gear box 81, and specifically concentrically through an engagement hub 110 as shown in FIGS. 7 and 8, a cutting assembly main drive shaft operatively extends. The cutting assembly main drive shaft comprises two primary sections, namely: a) a threaded drive screw or "worm" 115 shown in FIG. 11, which is an intermediate section that extends through the engagement hub 110; and b) an oscillation shaft 130, also shown in FIG. 11, and which is the inner most section and extends through the worm 115.

Turning first to the engagement hub 110, shown in FIG. 8, it is an outer most section that preferably extends downwardly from the gear box 81 and is structured to be matingly, and preferably threadingly engaged within the threaded aperture 58 formed in the main housing 51. As such, the engagement hub 110 functions to secure the drive means 80 to the cutting head assembly 50. Further, it will be recognized that the drive means 80 are thereby permitted to enter the cutting head assembly 50 through a top surface 56' and are thus, generally vertically disposed. It is believed that this feature results in less interference with the surgical field and facilitates finer handling by the surgeon than is offered by conventionally known microkeratomes. Specifically, known microkeratomes have typically provided for horizontally disposed drive means, which resulted in the surgeon having to handle a cord of the driving means, which if not held properly could cause drag on the operation of the microkeratome and/or result in a different pressure being applied to the microkeratome. Moreover, the structure of the present invention maintains its center of gravity substantially over the center of the eye, unlike old systems, thereby providing increased balance and ensuring that the cutting head assembly does not inadvertently tip away from the surface of the eye during use.

As illustrated in FIG. 8, the oscillation shaft also extends from the gear box 81. Turning now to FIG. 11, the oscillation shaft 130, which extends into the housing 51 through its aperture 58, is preferably an independent element that extends concentrically through and protrudes from both ends of the worm 115. The oscillation shaft 130, which is preferably structured to freely rotate relative to the worm 115 includes an upper drive portion 132 which may be welded onto shaft 130 but which is in any event, drivingly engaged with a main drive gear 102 secured to the motor main drive shaft 101. Accordingly, rotation of the motor main drive shaft 101 results in corresponding rotation of the oscillation shaft 130. Further, protruding off center from an opposite end 134 of the oscillation shaft 130 is an oscillation pin 135. The oscillation pin 135, which is preferably downwardly biased to maintain engagement pressure on the cutting element 70 is structured to extend into a slot 72' formed in an upper surface of the blade holder 72. As such, upon axial rotation of the oscillation shaft 130, the oscillation pin 135 rotates a predetermined radius off center and alternatingly engages opposite side edges of the slot 72' of the blade holder 72 to result in alternating, oscillating movement of the blade holder 72 and the cutting element 70 held thereby.

The oscillating shaft 130 further includes a secondary drive portion 133. The secondary drive portion 133 is drivingly connected with a first interior drive gear 103 contained within the gear box 81. The first interior drive gear 103 is connected with and drivingly secured to an interior drive shaft 104, which preferably includes a second interior drive gear 105 disposed thereon in spaced apart relation from the first interior drive gear 103. As such, upon rotation of the oscillation shaft 130, the second interior drive gear 105 also rotates.

Drivingly connected with the second interior drive gear 105 and structured to extend from an interior of the gear box 81, concentrically through the engagement hub 110, is the threaded drive screw or "worm" 115. The worm 115, which extends up into the gear box 81 includes a drive head 116 which engages the second interior drive gear 105. As a result, upon rotation of the interior drive shaft 104, the worm 115 correspondingly rotates within the housing 51 of the cutting head assembly 50. Further, rotatably disposed within the housing 51, in operative engagement with the worm 115, is a worm gear 120. The worm gear 120 preferably includes an increase diameter central portion 122 having a plurality of drive recesses formed about a perimeter thereof and structured to engage the exterior threaded surface of the worm 115 such that the central portion 122, and accordingly the entire worm gear 120, rotates about a horizontal axis as a result of the rotation of the worm 115 about a vertical axis. It is noted that the screw-like threaded surface of the worm 115 enables the worm 115 to rotate without moving vertically and successively engage the drive recesses on the worm gear 120 to effect rotation thereof. Extending from at least one, but preferably both vertical faces of the central portion 122 of the worm gear 120 is a propulsion shaft 125. The propulsion shaft 125, which comprises additional tracking means, is structured to protrude from the sidewall structure 53 of the main housing 51 and engage the toothed track 43 on the positioning ring 32 such that upon rotation of the worm gear 120, and accordingly rotation of the propulsion shaft 125, the propulsion shaft 125 rides along the toothed track 43 and drives the cutting head assembly 50 across the positioning ring 32 smoothly and at a steady and defined pace. Furthermore, it is seen that by reversing the rotational direction of the interior drive shaft 101 within the gear box 81, the direction of rotation of the worm 115 and therefore the worm gear 120 are reversed to effectuate reverse driven movement of the cutting head assembly 50 over the positioning head 32. Also, so as to facilitate movement over toothed track 43 and the arcuate path thereof, it is preferred that the propulsion shaft 125 portion of the worm gear 120 include a helical gear configuration or plurality of angled ridges to permit more effective alignment with the curved toothed track 43 and movement thereover.

Referring once again to the motor 100, it is preferred that it be controlled by a foot pedal or like actuation means. In the case of a foot pedal, it is preferred that it be a dual function foot pedal such that one side will function to drive the motor main drive gear 101, and therefore the cutting head assembly 50 in a forward direction, and the second side will drive them in a reverse direction. Further, the system may be set to a manual mode whereby a doctor must affirmatively reverse the direction of movement, or an "auto-reverse" mode wherein upon the cutting head assembly 50 traveling its maximum distance it automatically reverses direction. In either case, however, the motor 100 will preferably be equipped with a sensor to detect an abrupt current increase. Specifically, when the cutting head assembly 50 reaches the stop means 65 and further forward movement is either partially or completely resisted, an abrupt current increase will occur in the motor 100. That abrupt current increase, once detected, can signal either the power to shut off, or the reverse movement to commence, depending upon a doctor's desired setting.

Finally, it will be appreciated that the present invention can be utilized on both eyes of the patient. Specifically, as worm gear 120 runs through housing 51 and juts out of the opposite surrounding sidewall structure 53 of housing 51, the cutting head assembly is ready to use on the opposite eye of a patient. In order to accomplish this, and due to the symmetric shape of the cutting head assembly 50, the drive means 80 need only be removed from the housing 51 and thus, coupling member 90, whereupon, it can be re-oriented 180 degrees for use with the opposite eye of a patient.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A surgical device for cutting across a cornea of an eye of a patient, said device comprising:
   a) a positioning ring structured to be at least temporarily attached to a portion of the eye surrounding the cornea to be cut; said positioning ring defining an aperture to receive and expose the cornea to be cut;
   b) said positioning ring including a guide assembly defining a generally arcuate path; and
   c) a cutting head assembly including a cutting element for cutting the cornea;
   d) said cutting head assembly further including a nose segment structured to applanate the cornea to be cut; said nose segment structured to move in unison at substantially all times with said cutting head assembly over said positioning ring along said generally arcuate path defined by said guide assembly.

2. A surgical device as recited in claim 1 wherein said cutting head assembly further includes a depth adjusting assembly structured to adjust a depth at which said cutting element cuts into the cornea.

3. A surgical device for cutting across a cornea of an eye of a patient, said device comprising:
   a) a positioning ring structured to be at least temporarily attached to a portion of the eye surrounding the cornea to be cut; said positioning ring defining an aperture to receive and expose the cornea to be cut;
   b) said positioning ring including a guide assembly defining a generally arcuate path; and
   c) a cutting head assembly including a cutting element for cutting the cornea;
   d) said cutting head assembly further including a nose segment structured to applanate the cornea to be cut; said nose segment structured to move in unison at substantially all times with said cutting head assembly in both a forward and a reverse direction over said positioning ring along said generally arcuate path defined by said guide assembly.

4. A surgical device as recited in claim 3 wherein said cutting head assembly further includes a depth adjusting assembly structured to adjust a depth at which said cutting element cuts into the cornea.

5. A surgical device for cutting across a cornea of an eye of a patient, said device comprising:
   a) a positioning ring structured to be at least temporarily attached to a portion of the eye surrounding the cornea to be cut; said positioning ring defining an aperture to receive and expose the cornea to be cut;
   b) said positioning ring including a guide track defining a generally arcuate path; and
   c) a cutting head assembly including a cutting element for cutting the cornea, said cutting head assembly being structured to move along said generally arcuate path defined by said guide track.

6. A surgical device as recited in claim 5 wherein said cutting path defined by said guide track terminates at an upper portion of the cornea of both the patient's left and right eye.

7. A surgical device as recited in claim 5 wherein said cutting head assembly is structured for automated movement along said generally arcuate path.

8. A surgical device for cutting substantially across a cornea of an eye of a patient, said device comprising:
   a) a positioning ring structured to be at least temporarily attached to a portion of the eye surrounding the cornea to be cut
   b) a cutting head assembly including a cutting element for cutting the cornea; and
   c) a drive assembly operably connected to said cutting head assembly from generally a vertical orientation for causing movement of said cutting head assembly across said positioning ring in a direction transverse to a line defined by a cutting edge of said cutting element.

9. A surgical device for cutting substantially across a cornea of an eye of a patient, said device comprising:
   a) a positioning ring structured to be at least temporarily attached to a portion of the eye surrounding the cornea to be cut; said positioning ring defining an aperture;
   b) said positioning ring including a guide assembly defining a generally arcuate path; and
   c) a cutting head assembly including a cutting element for cutting the cornea;
   d) a drive assembly operably connected to said cutting head assembly from generally a vertical orientation for causing movement of said cutting head assembly across said positioning ring and for causing oscillating movement of said cutting element.

10. A surgical device for cutting substantially across a cornea of an eye of a patient, said device comprising:
    a) a positioning ring structured to be at least temporarily attached to a portion of the eye surrounding the cornea to be cut; said positioning ring defining an aperture;
    b) said positioning ring including a guide assembly defining a generally arcuate path;
    c) said guide assembly including at least a post member which defines a rotation axis of said generally arcuate path;
    d) a cutting head assembly including a cutting element for cutting the cornea; and
    e) a drive assembly operably connected to said cutting head assembly from generally a vertical orientation for causing movement of said cutting head assembly across said positioning ring.

11. A surgical device for cutting substantially across a cornea of an eye of a patient, said device comprising:
    a) a positioning ring structured to be at least temporarily attached to a portion of the eye surrounding the cornea to be cut; said positioning ring defining an aperture;
    b) said positioning ring including a guide assembly defining a generally arcuate path;
    c) said guide assembly including at least a guide track;
    d) a cutting head assembly including a cutting element for cutting the cornea; and
    e) a drive assembly operably connected to said cutting head assembly from generally a vertical orientation for causing movement of said cutting head assembly across said positioning ring and for causing oscillating movement of said cutting element.

12. A surgical device for cutting substantially across a cornea of an eye of a patient, said device comprising:
    a) a positioning ring structured to be at least temporarily attached to a portion of the eye surrounding the cornea to be cut; said positioning ring defining an aperture;
    b) said positioning ring including a guide assembly defining a generally arcuate path;
    c) said guide assembly including at least a post member structured to define a rotation axis of said generally arcuate path, and a guide track;
    d) a cutting head assembly including a cutting element for cutting the cornea and operatively coupled to said post member; and
    e) a drive assembly operably connected to said cutting head assembly from generally a vertical orientation for causing movement of said cutting head assembly across said positioning ring and for causing oscillating movement of said cutting element.

13. A surgical device for cutting across a cornea of an eye of a patient, said device comprising:
    a) a positioning ring structured to be at least temporarily attached to a portion of the eye surrounding the cornea to be cut; said positioning ring defining an aperture to receive and expose the cornea to be cut;
    b) said positioning ring including a guide assembly defining a generally arcuate path;
    c) said guide assembly including a guide track;
    d) a cutting head assembly including a cutting element for cutting the cornea, said cutting head assembly being structured to move along said generally arcuate path defined by said guide assembly; and
    e) at least said guide track structured to maintain said cutting head assembly in engaging relation with said positioning ring during movement of said cutting head assembly along said generally arcuate path.

14. A surgical device for cutting across a cornea of an eye of a patient, said device comprising:
    a) a positioning ring structured to be at least temporarily attached to a portion of the eye surrounding the cornea to be cut; said positioning ring defining an aperture to receive and expose the cornea to be cut;
    b) said positioning ring including a guide assembly defining a generally arcuate path, said guide assembly including a channel member and a post member;
    c) a cutting head assembly including a cutting element for cutting the cornea, at least said channel member and said post member structured to guide said cutting head assembly across the eye along said generally arcuate path.

15. A surgical device for cutting substantially across a cornea of an eye of a patient, said device comprising:
    a) a positioning ring structured to be at least temporarily attached to a portion of the eye surrounding the cornea to be cut; said positioning ring defining an aperture;
    b) said positioning ring including a guide assembly defining a generally arcuate path;
    c) a cutting head assembly including a cutting element for cutting the cornea; and
    d) a drive assembly operably connected to said cutting head assembly from a generally vertical orientation for causing oscillating movement of said cutting element.

* * * * *